(12) United States Patent
Morrison et al.

(10) Patent No.: US 6,292,700 B1
(45) Date of Patent: Sep. 18, 2001

(54) ENDOPELVIC FASCIA TREATMENT FOR INCONTINENCE

(75) Inventors: George A. Morrison, Foster City; Garry L. Carter, Pleasanton; Timothy G. Dietz, Fremont, all of CA (US)

(73) Assignee: SURx, Inc., Pleasanton, CA (US)

( * ) Notice: Subject to any disclaimer, the term of this patent is extended or adjusted under 35 U.S.C. 154(b) by 0 days.

(21) Appl. No.: 09/413,100

(22) Filed: Oct. 6, 1999

Related U.S. Application Data
(60) Provisional application No. 60/153,330, filed on Sep. 10, 1999.

(51) Int. Cl.[7] .................................................... A61F 7/12
(52) U.S. Cl. .............................. 607/98; 607/101; 606/41
(58) Field of Search .............................. 607/96, 98–102, 607/113; 606/27–33

(56) References Cited

U.S. PATENT DOCUMENTS

| 373,399 | 11/1887 | Hamilton . |
|---|---|---|
| 3,575,158 | 4/1971 | Summers . |

(List continued on next page.)

FOREIGN PATENT DOCUMENTS

| WO 93/07815 | 4/1993 | (WO) . |
| WO 96/00041 | 1/1996 | (WO) . |
| WO 96/00042 | 1/1996 | (WO) . |
| WO 97/15238 | 5/1997 | (WO) . |
| WO 97/32532 | 9/1997 | (WO) . |
| WO 97/39688 | 10/1997 | (WO) . |
| WO 97/43970 | 11/1997 | (WO) . |
| WO 97/43971 | 11/1997 | (WO) . |
| WO 98/07468 | 2/1998 | (WO) . |
| WO 98/38936 | 9/1998 | (WO) . |
| WO 00/18314 | 4/2000 | (WO) . |

OTHER PUBLICATIONS

Hayes et al., "Prediction of Transient Temperature Fields and Cumulative Tissue Destruction for Radio Frequency Heating of a Tumor," *Medical Physics*, University of Texas, Austin, Texas; 12 (6):1985.

*Primary Examiner*—Roy Gibson
(74) *Attorney, Agent, or Firm*—Townsend Townsend & Crew LLP; Mark D. Barrish, Esq.

(57) ABSTRACT

Methods, devices, and systems for treating the support structures of the body, particularly for incontinence, take advantage of two mechanisms to enhance the support provided by the fascia, ligaments and tendons: first, the invention increases a modulus of elasticity of these tissues, and particularly of the fascial tissues. The increase in modulus can be effected by directing sufficient energy to the fascial tissue so as to promote the formation of scar tissue. The second mechanism attaches tissue planes together, often by directing energy to an interface between adjacent fascial tissues.

25 Claims, 7 Drawing Sheets

U.S. PATENT DOCUMENTS

| | | |
|---|---|---|
| 3,749,098 | 7/1973 | De Bennetot . |
| 3,924,631 | 12/1975 | Mancusi, Jr. . |
| 3,926,175 | 12/1975 | Allen et al. . |
| 3,939,821 | 2/1976 | Roth . |
| 4,311,145 | 1/1982 | Esty et al. . |
| 4,409,453 | 10/1983 | Smith . |
| 4,453,536 | 6/1984 | Abild . |
| 4,686,962 | 8/1987 | Haber . |
| 4,765,331 | 8/1988 | Petruzzi et al. . |
| 4,773,393 | 9/1988 | Haber . |
| 4,776,344 | 10/1988 | Shirasaki et al. . |
| 4,802,479 | 2/1989 | Haber et al. . |
| 4,807,620 | 2/1989 | Strul et al. . |
| 4,832,680 | 5/1989 | Haber . |
| 4,911,149 * | 3/1990 | Borodulin et al. . |
| 4,994,019 | 2/1991 | Fernandez et al. . |
| 5,012,822 | 5/1991 | Schwarz . |
| 5,035,696 | 7/1991 | Rydell . |
| 5,041,109 | 8/1991 | Abela . |
| 5,057,106 | 10/1991 | Kasevich et al. . |
| 5,098,429 | 3/1992 | Sterzer . |
| 5,103,804 | 4/1992 | Abele et al. . |
| 5,140,999 | 8/1992 | Ardito . |
| 5,190,517 | 3/1993 | Zieve et al. . |
| 5,201,732 | 4/1993 | Parins et al. . |
| 5,234,409 | 8/1993 | Goldberg et al. . |
| 5,256,133 | 10/1993 | Spitz . |
| 5,281,217 | 1/1994 | Edwards et al. . |
| 5,281,218 | 1/1994 | Imran . |
| 5,282,799 | 2/1994 | Rydell . |
| 5,293,869 | 3/1994 | Edwards et al. . |
| 5,304,123 | 4/1994 | Atala et al. . |
| 5,309,910 | 5/1994 | Edwards et al. . |
| 5,314,465 | 5/1994 | Maurer et al. . |
| 5,314,466 | 5/1994 | Stern et al. . |
| 5,366,490 | 11/1994 | Edwards et al. . |
| 5,370,671 * | 12/1994 | Maurer et al. .................. 607/41 |
| 5,370,675 | 12/1994 | Edwards et al. . |
| 5,370,677 | 12/1994 | Rudie et al. . |
| 5,370,678 | 12/1994 | Edwards et al. . |
| 5,376,064 | 12/1994 | Cerny . |
| 5,385,544 | 1/1995 | Edwards et al. . |
| 5,403,312 | 4/1995 | Yates et al. . |
| 5,405,346 | 4/1995 | Grundy et al. . |
| 5,411,475 | 5/1995 | Atala et al. . |
| 5,431,649 | 7/1995 | Mulier et al. . |
| 5,437,603 | 8/1995 | Cerny et al. . |
| 5,437,664 | 8/1995 | Cohen et al. . |
| 5,447,529 | 9/1995 | Marchlinski et al. . |
| 5,454,809 | 10/1995 | Janssen . |
| 5,458,596 | 10/1995 | Lax et al. . |
| 5,462,545 | 10/1995 | Wang et al. . |
| 5,496,312 | 3/1996 | Klicek . |
| 5,514,130 | 5/1996 | Baker . |
| 5,533,999 | 7/1996 | Hood et al. . |
| 5,556,396 | 9/1996 | Cohen et al. . |
| 5,569,242 | 10/1996 | Lax et al. . |
| 5,588,960 * | 12/1996 | Edwards et al. ................ 604/20 |
| 5,609,598 | 3/1997 | Laufer et al. . |
| 5,667,615 * | 9/1997 | Maurer et al. ................ 156/242 |
| 5,697,281 | 12/1997 | Eggers et al. . |
| 5,697,536 | 12/1997 | Eggers et al. . |
| 5,697,882 | 12/1997 | Eggers et al. . |
| 5,697,909 * | 12/1997 | Eggers et al. ................ 604/114 |
| 5,810,847 | 9/1998 | Laufer et al. . |
| 5,957,920 * | 9/1999 | Baker .............................. 606/33 |
| 6,081,749 | 6/2000 | Ingle et al. . |
| 6,086,549 * | 7/2000 | Neese et al. .................... 600/587 |
| 6,090,856 * | 7/2000 | Sasaki ............................. 514/646 |
| 6,091,995 * | 7/2000 | Ingle et al. .................... 607/138 |
| 6,139,569 * | 10/2000 | Ingle et al. .................... 607/104 |
| 6,156,060 * | 12/2000 | Roy et al. ...................... 607/113 |

* cited by examiner

ENDOPELVIC FASCIA TREATMENT FOR INCONTINENCE

CROSS-REFERENCES TO RELATED APPLICATIONS

This application claims the benefit and priority of U.S. Provisional Patent Application No. 60/153,330 filed Sep. 10, 1999, the full disclosure of which is incorporated herein by reference for all purposes.

BACKGROUND OF THE INVENTION

1. Field of the Invention

The present invention generally relates to medical devices, methods, and systems, particularly for the treatment of urinary incontinence.

Urinary incontinence arises in both men and women with varying degrees of severity, and from different causes. In men, the condition frequently occurs as a result of prostatectomies which result in mechanical damage to the urinary sphincter. In women, the condition typically arises after pregnancy when musculoskeletal damage has occurred as a result of inelastic stretching of the structures supporting the genitourinary tract. Specifically, pregnancy can result in inelastic stretching of the pelvic floor, the external sphincter, and the tissue structures which support the bladder, urethra, and bladder neck region. In each of these cases, urinary leakage typically occurs when a patient's abdominal pressure increases as a result of stress, e.g., coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt a behavior modification intended to reduce the incidence of urinary leakage.

In cases where such non-interventional approaches are inadequate or unacceptable, the patient may undergo surgery to correct the problem. A wide variety of procedures have been developed to correct urinary incontinence in women. Several of these procedures are specifically intended to support the bladder neck region. For example, sutures, straps or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

In work done related to the present invention, it has been proposed to treat urinary incontinence by selectively contracting or shrinking a portion of the pelvic support tissue so as to reposition the bladder and/or urogenital tract. U.S. patent application Ser. No. 08/910,370, now U.S. Pat. No. 6,091,995, generally describes laparoscopic and other minimally invasive devices, methods, and systems for shrinking tissues, particularly for treatment of incontinence. U.S. patent application Ser. No. 09/133,496, now U.S. Pat. No. 6,216,704, describes noninvasive. devices, methods, and systems for shrinking of tissues, often by cooling a surface of an intermediate tissue and directing energy through the cooled intermediate tissue to the target tissue so as to effect shrinkage. U.S. patent application Ser. No. 09/170,767, now U.S. Pat. No. 6,156,060, is directed to static devices and methods to shrink tissues for incontinence. Finally, U.S. Pat. No. 09/103,352, now U.S. Pat. No. 6,044,847, describes tuck and fold fascial shortening for incontinence. Each of these applications is assigned to the present assignee, and their full disclosures are incorporated herein by reference.

While these recent proposals for treatment of incontinence represent significant advancements in the art, treatment of incontinence and other conditions related to insufficient tissue support could benefit from still further advances. In particular, it is generally beneficial to minimize collateral damage imposed on the treated and adjacent tissues during any therapy. It would further be beneficial to provide alternative treatment mechanisms for reducing or eliminating the severity and occurrence of incontinence events.

A variety of other problems can arise when tissues of the body fail to provide adequate support. Weakened pelvic support tissues (particularly the ligaments and fascia of the pelvic area) can lead to a variety of ailments including, for example, cystocele, prolapse, and the like. Cosmetic surgeries are also often performed to enhance the support provided by fascial tissues. For example, abdominoplasty (often called a "tummy tuck") is often performed to enhance support provide by the abdominal wall. The distortion of these support tissues may be due to strain, advanced age, congenital predisposition, or the like.

For these reasons, it would be desirable to provide improved devices, methods, and systems for treating the support tissues of the body. It would be particularly desirable to provide techniques for treatment of incontinence and other conditions by enhancing the support of the body's own tissue systems. It would further be advantageous if these improved techniques could take advantage of the recent advancements in minimally invasive and noninvasive therapies described hereinabove, and could effect treatment with decreased collateral damage. Some or all of these advantages are provided by the invention described hereinbelow.

2. Description of the Background Art

U.S. patent application Ser. Nos. 08/910,370, 09/133,496, 09/170,767, and 09/103,352 are described hereinabove. PCT Application No. 97/43,971 describes a method and apparatus for ablating turbinates. PCT Application No. 98/38,936 describes a method and apparatus for treating venous insufficiency. The impact of surgical treatments of the urethra were described by Shlomo Raz in FEMALE UROLOGY, $2^{nd}$ Ed. (1996). This reference also describes techniques of surgical repair for treatment of cystocele on pages 340–342, while various alternative known surgical interventions for treatment of incontinence are schematically illustrated on page 356. At least some of these procedures are also described in FEMALE PELVIC DISORDERS, STAGNATION AND MANAGEMENT by J. Thomas Benson (1992) on pages 239–240.

An electrosurgical probe for the controlled contraction of tissues of joints and for dermatological indications is described in U.S. Pat. No. 5,458,596. A bipolar electrosurgical probe having electrodes formed over a restricted arc of its distal end for treatment of, for example, the esophagus, is described in U.S. Pat. No. 4,765,331. Systems and methods for electrosurgical cutting and ablation are described in U.S. Pat. No. 5,697,882. Methods and apparatus for controlled contraction of soft tissues is described in U.S. Pat. No. 5,569,242. U.S. Pat. No. 5,423,811 describes a method for RF ablation using cooled electrodes.

SUMMARY OF THE INVENTION

The present invention provides improved methods, devices, and systems for treating the support structures of the body, as a treatment for incontinence and other conditions. In general, the invention takes advantage of two mechanisms to enhance the support provided by the fascia, ligaments and tendons: first, the invention increases a modulus of elasticity of these tissues, and particularly of the fascial tissues. The increase in modulus can be effected by directing sufficient energy to the fascial tissue so as to promote the formation of scar tissue. The resulting scarred tissue is generally significantly less elastic than the original fascia, and may also have an increased thickness (either as the result of fascial shrinkage or from the proliferation of scar tissue and/or smooth muscle cells). This local increase in modulus of the scarred support tissue can transfer stress and strain from the area of treatment to adjoining areas, and may also shorten the response time of the tissue plane to stress pulses (such as those which might result in incontinence events).

The second mechanism encompassed by the invention for enhancing the support is to promote attachment of adjacent support tissues to each other. Adjacent fascial tissue surfaces in the pelvic support system are often able to slide freely against each other. This free lateral movement allows the visceral organs to expand and contract over time. However, if there is inadequate support, the motion may become extreme and result in incontinence, prolapse, and other conditions. By directing energy (for example) at the interface between sliding fascial tissue surfaces, the relative motion at the interface can be restricted so as to enhance support of the pelvic viscera. Heating may be used to induce acute (through tissue fusion) and/or chronic (through the growth of cross-linked collagenated tissue or adhesions) attachments between the tissues.

In a first aspect, the invention provides a method for treating incontinence. The method comprises reducing an elasticity of a pelvic support tissue system sufficiently so that the tissue system inhibits incontinence. Generally, the elasticity will be reduced by promoting scarring of fascia supporting the urethra and/or bladder. The scarring reduces the modulus of elasticity of the fascial tissue so that the fascial tissue inhibits incontinence. Such scarring will preferably be promoted by directing energy into the fascial tissue so as to injure the fascial tissue without ablating the fascial tissue. While such energy can be delivered in the form of ultrasound, microwave, laser, or thermal conduction, it will preferably be in the form of an RF current conducted through the tissue so that the tissue's impedance effects heating.

Advantageously, heating the fascial tissue to a temperature of about 45° C. or more is sufficient to promote the formation of scar tissue and thereby decrease elasticity. Hence, elasticity can be reduced by heating the tissue below the temperatures generally used to effect contraction or shrinkage (typically over about 60° C.). These lower tissue temperatures can significantly reduce collateral damage, particularly where the elasticity of the tissue is reduced without significant shrinkage. As elasticity reduction and shrinking represent two distinct structural alterations in the tissue system, they may be applied independently or in selective combinations so as to provide the desired change in structural support.

Typically, the elasticity of the tissue is reduced along a length of tissue. The tissue will be susceptible to loading along this length by an incontinence-event stress such as coughing, laughing, exercise, or the like. Reduction in the elasticity may be provided with or without selective reduction in the length (typically by collagenous tissue shrinkage). The present invention allows selective tailoring of an incontinence therapy in response to a comparison between a change in urethral pressure relative to a change in vesical pressure during an incontinence event stress pulse.

A variety of tissues and tissue structures may be targeted for the present incontinence treatments. These include the tissue structures and systems of the pelvic floor and/or diaphragm, bladder and urethra, vagina, uterus, bowel, and the like. Treatment modalities include thermal, electrosurgical, laser, focused ultrasound or microwave, and a variety of bioactive or biochemical agents including local drug delivery, caustic compounds, pleurodesis agents, sclerosing agents, growth factors, surgical sealants, and/or the like. When bioactive agents are used, the invention may employ any of a wide variety of available compounds being marketed.

In another aspect, the invention provides a method for treating incontinence. The method comprises promoting attachment between a first tissue and second tissue with energy or an active agent. The second tissue slidingly engages the first tissue prior to attachment, so that the attachment limits motion between the first and second tissues. The limited relative motion of these tissues inhibits incontinence.

Preferably, the attachment promoting step comprises directing sufficient energy to an interface between the first tissue and second tissue to injure a fascial tissue surface without ablating the fascial tissue. The invention encompasses a variety of energy directing mechanisms, with the preferred energy comprising RF current transmitted to the fascial tissue. Typically, first and second fascial tissue surfaces of the first and second tissue will be heated. The heat may acutely fuse the tissue surfaces together. Optionally, collagen of the first and second tissues will be cross-linked during the healing process. In other embodiments, the attachment promoting step may result in the formation of adhesions between the first and second tissues. Surprisingly, although the prevention of adhesion formation is an important goal of many pelvic surgeries, controlled adhesion generation may result in significant patient benefit where the adhesion serves to enhance the support of the pelvic viscera.

In another aspect, the invention provides a method for treating incontinence. This method comprises measuring a urethral pressure and a vesicle pressure during a stress. A change in the measured urethral pressure is compared relative to a change in the measured vesicle pressure. An elasticity of a pelvic support system is reduced in response to the comparing step sufficiently that the urethral pressure will remain greater than the vesicle pressure during stress.

In yet another aspect, the invention provides a system to treat incontinence. The system comprises a probe for delivering energy or an active agent to a pelvic support tissue so as to reduce an elasticity of the pelvic support tissue. A control system is coupled to the probe. The control system limits the delivery from the probe to avoid collateral damage.

In many embodiments, the control system will limit an amount of the energy or the agent to avoid shrinkage of the tissue. The probe will preferably comprise an energy delivery member, ideally comprising an RF electrode. The exemplary system further includes a urethral pressure sensor, a vesicle pressure sensor, and a processor coupled to the urethral and vesicle pressure sensors. The processor generates an output indicating a change in urethral pressure relative to a change in vesicle pressure. This output is particularly useful for determining the desired reduction in elasticity of the pelvic support tissue.

In another aspect, the invention provides a kit for treating incontinence. The kit comprises a probe for directing energy or a bioactive agent to a pelvic tissue system. Instructions for using the probe will describe methods for enhancing structural support provided by the tissue system so that incontinence is inhibited. The instructions and probe may be packaged together, and the method steps of the instructions may be any of the methods described herein.

DESCRIPTION OF THE SPECIFIC EMBODIMENTS

The present invention generally provides methods, devices, and systems which enhance the structural support provided by a body's tissues, particularly as a therapy for incontinence. The techniques of the invention will generally involve promoting the formation of scar tissue so as to stiffen a tissue structure, and/or the attachment of two adjacent tissues (which are normally free to slide relative to each other) to each other. Energy may be directed from a probe into one or more fascial tissues of the pelvic support system. The energy may lead to the formation of stiff scar tissue, and/or it may attach adjacent fascial tissues together by fusing, cross-linking of collagen, the formation of adhesions, or the like. Optionally, the energy may also cause contraction of the fascial tissue by heating this collagenous layer to a contraction temperature over about 60° C. Alternatively, stiffening and/or attachment of adjacent fascial layers may be provided without significant contraction, as scar tissue can be promoted by heating the fascia to temperature below that at which significant contraction takes place, for example, over about 45° C.

As these techniques will be effective for controllably and repeatably enhancing the structural support of a wide variety of fascia and other collagenous tissues through the body, they will find applications in a wide variety of therapies, including cosmetic applications, orthopedic applications, treatment of hernias, and the like. However, the most immediate application for the invention will be to enhance a tissue system's support of the bladder, bladder neck region, and urethra so as to inhibit urinary incontinence, generally without sutures, slings, fasteners, or other artificial structures.

The techniques of the present invention will often be used to stiffen or attach fascia, tendons, and other collagenous tissues, preferably without ablation of these collagenous tissues. As used herein, this means that collagenous tissues are not removed and their function (particularly their structural support function) is not destroyed. Histologically, some tissue necrosis may occur, and the structural strength of the tissues may initially decrease immediately after treatment. Nonetheless, the treated tissues will generally continue to provide at least some structural support, and their structural strength should increase during the healing process so that the healed tissue has preferably the same ultimate structural strength as, and often greater stiffness (for example, having a higher modulus of elasticity so as to stretch less under tension) than before treatment.

Figure 1:
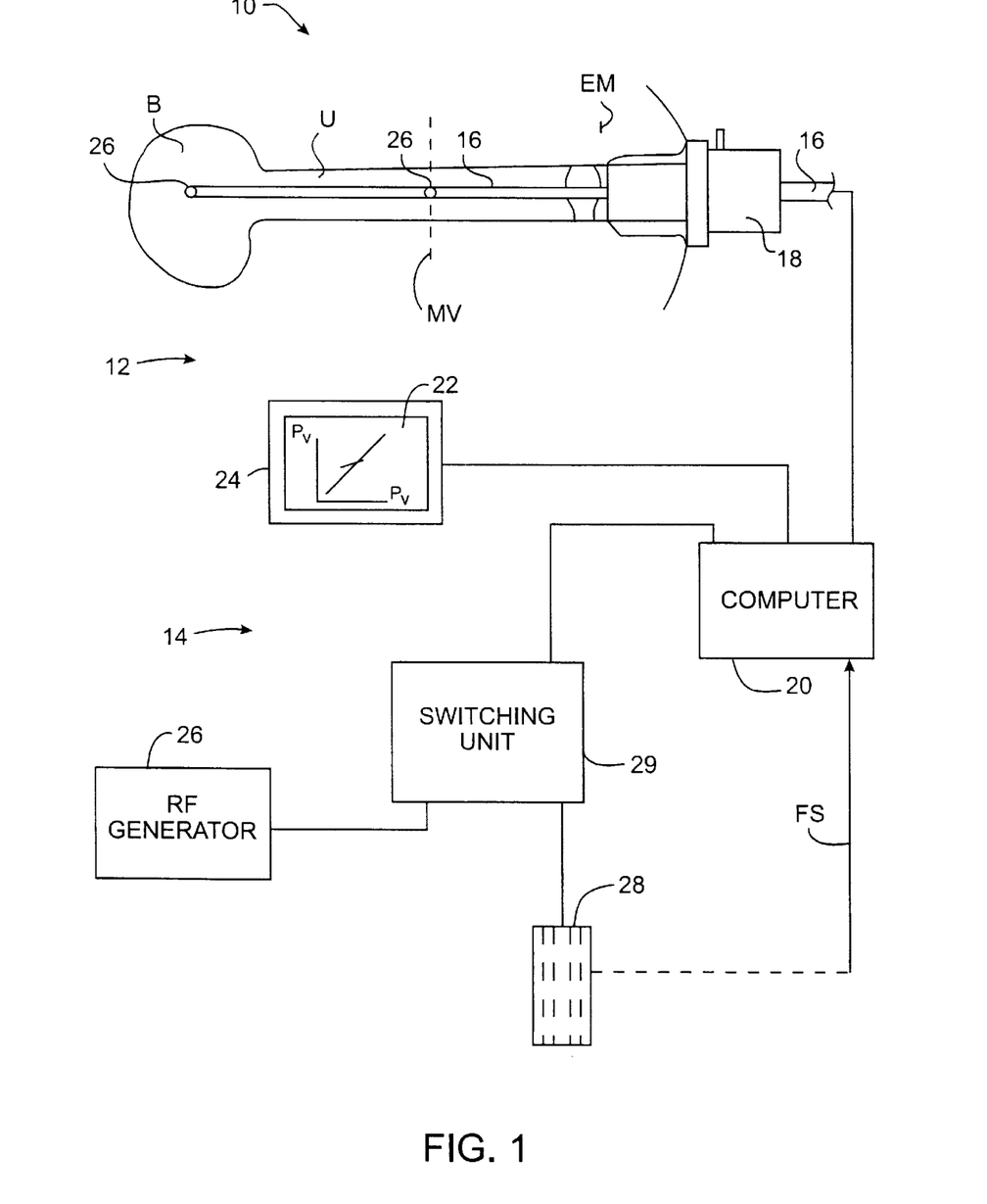
FIG. 1 is a schematic illustration of a diagnosis and treatment system for urinary incontinence, according to the principles of the present invention.

Referring now to FIG. 1, a urinary incontinence diagnosis and treatment system 10 generally includes a diagnostic subsystem 12 for diagnosing stress incontinence and a treatment subsystem 14 which provides a therapy for a specific patient in response to a specific diagnosis. Diagnostic system 12 generally includes a catheter 16 for sensing pressures in bladder B and in urethra U, and a holder 18 which helps keep the catheter in position when the bladder and urethra move during a pressure pulse. Signals from catheter 16 are transmitted to processor 20, which displays a pressuregram 22 on display 24. Pressuregram 22 indicates a change in urethral pressure relative to a change in vesicular pressure.

Diagnostic system 12 is described more fully in co-pending U.S. patent application Ser. No. 09/288,865, filed on Mar. 9, 1999, and in Provisional Application No. 60/104,818, filed on Oct. 19, 1998, the full disclosures of which are incorporated by reference. In general, catheter 16 includes pressure sensors 26. Pressure sensors 26 sense vesicular pressure within bladder B, and sense a maximum urethral pressure within urethra U, with the location of this maximum urethral pressure sometimes being referred to as the mid-urethra MU. To maintain the location of catheter 16 during a pressure pulse, holder 18 supports the catheter while allowing the catheter to move with the external meatus EM.

To maintain the position of catheter 16 within urethra U, the catheter may include a balloon which generally engages the surrounding urethra, or holder 18 may include a surface which engages, and which supports the catheter relative to, the external meatus EM. This allows catheter 16 to provide pressure signals which accurately reflect the urethral and vesicular pressure throughout a pressure pulse, which may be induced by having a patient cough, by applying an external impulse against the patient's abdomen, or the like. Processor 20 can record these pressures throughout multiple pressure pulses for displaying as pressuregram 22. Generally, where urethral pressure remains higher than vesicular pressure (above the $P_u=P_v$ line on the pressuregram) leakage will not occur. However, where vesicular pressure increases faster than urethral pressure during a pressure pulse, a sufficiently strong pulse may produce leakage.

To increase the rate of change of the urethral pressure for each increment of change in the vesicular pressure, treatment system 14 may be employed to increase a modulus of the patient's pelvic support system. Often, treatment system 14 will selectively promote formation of scar tissue along a fascial plane. Some of the components of treatment system 14 are substantially similar to those of the system described in co-pending U.S. patent application Ser. No. 09/170,767, the full disclosure of which is incorporated herein by reference. To remodel tissues of the pelvic support system, power supply 26 directs RF current to selected pairs of electrodes on probe 28 under the direction of processor 20. Here, selective heating commands from processor 20 are implemented by a separate switching unit 29. It should be understood that in alternative arrangements, the switching unit may be incorporated into processor 20, power supply 26, or probe 28, and that separate processors may be provided for the diagnostic and treatment subsystems. In many embodiments, feedback on the course of treatment will be provided in the form of feedback signals FS transmitted from probe 28 to processor 20.

Figure 2:
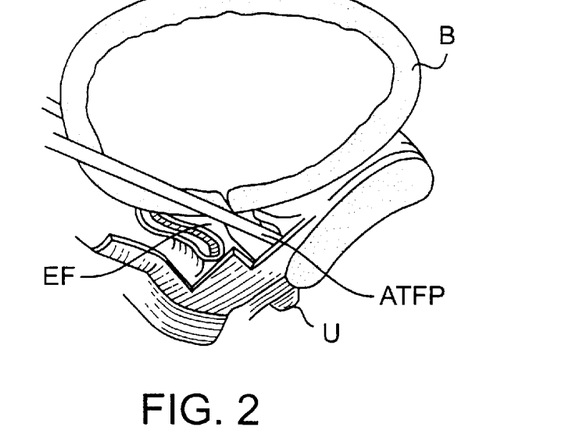
FIG. 2 is a cross-sectional view illustrating some of the pelvic support tissues which may be targeted for treatment by the system of FIG. 1.

The tissues of the pelvic support system, which generally maintains the position of much of the genitourinary tract, and in particular the position of urinary bladder B and urethra U, are illustrated in FIG. 2. In general, endopelvic fascial EF may define a hammock-like structure which extends laterally between the left and right arcus tendinous fascia pelvis ATFP. These lateral structures may extend substantially between the anterior and posterior portions of the pelvis, so that the endopelvic fascia EF largely defines the pelvic floor.

The fascial tissue of the pelvic floor may comprise tissues referred to under different names by surgeons of different disciplines, and possibly even by different practitioners within a specialty. In fact, some surgeons may assign a collagenous support structure of the endopelvic fascia one name when viewed from a superior approach, and a different name when viewed from an inferior approach. Some of the endopelvic fascia may comprise two collagenous layers with a thin muscular layer therebetween, or may comprise a single collagenous layer. The hammock-like endopelvic fascia described herein may be damaged or missing, particularly after pregnancy, so that the support of the genitourinary tract is instead provided by a variety of fascial layers, muscular tissues, ligaments, and/or tendons within the pelvis. Hence, the treatment of the present invention may be directed at a variety of tissue structures defining the pelvic floor and/or diaphragm (including: anterior sacrococcygeal ligament; arcs tendineus fasciae pelvis ATFP, the white line of the pelvis; fasciae of the obturator internus muscle; the arcs tendineus levator ani or "picket fence" to the iliococcygeus portion of the levator ani muscle; bulbocavernosus muscle; ischiocavernosus muscle; urethrovaginal sphincter; m. compressor urethrae muscle; and m. sphincter urethrovaginal muscle which replaces deep perineal muscle); structures of the bladder and urethra (including: urethrovesical fascia; detrusor muscle; and the pubo-coccygeus muscle which relaxes to open the bladder neck, initiating micturation); structures of the vagina (including: vagino-uterine fascia, lamina propria-the dense connective tissue layer just under the epithelium; pubourethral or puboprostatic ligaments; pubo-vesicle ligament and posterior pubo-urethral or puboprostatic ligament; pubovesicle muscle, a smooth muscle that is integrated with the pubovesicle ligament; and pubocervical fascia which attaches to the ATFP); structures of the uterus (including: round ligament; sacrouterine ligament; and broad ligament); and structures of the bowel (including: rectal fascia and mackenrodt's ligament).

Figure 3:
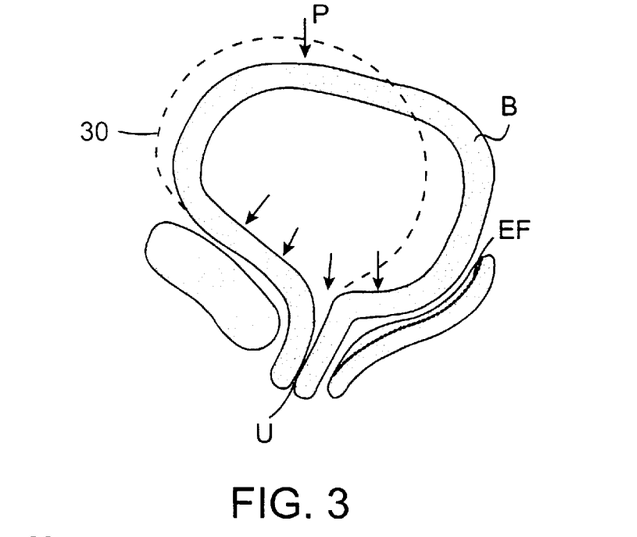
FIG. 3 is a schematic cross-sectional view illustrating how an excessively elastic pelvic support system can discharge when subjected to a pressure pulse.
Figure 4A:
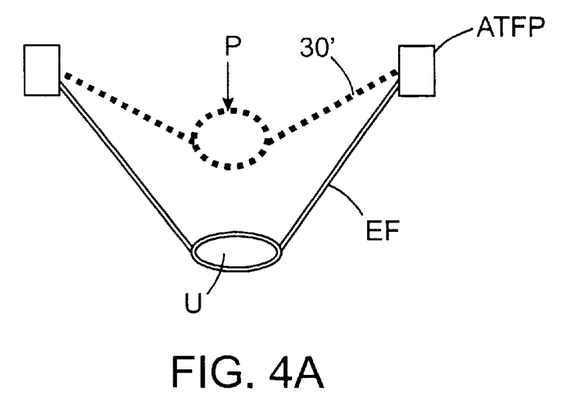
FIGS. 4A and B are alternative schematic illustrations showing how excessive elasticity of the pelvic support system can delay sealing forces against the urethra, thereby contributing to incontinence.
Figure 4B:
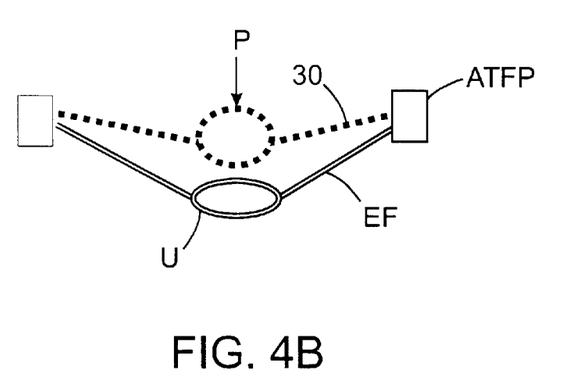

The effects of excessive elasticity of the pelvic support tissues are illustrated in FIGS. 3, 4A and 4B. In FIG. 3, a pressure pulse P moves bladder B from an initial position 30 to a lowered position as shown. As endopelvic fascia EF stretches excessively in this case, the fluid pressure within the bladder advances into the bladder neck and down urethra U. Leakage may result in part because the endopelvic fascia allows the bladder to drop below its initial position, at which fluid pressure within the bladder actually helps to seal the bladder neck. Perhaps even more importantly, stretching of the endopelvic fascia may alter the timing of pressure pulse transmission to urethra U.

When a continent woman coughs, the pressure in the urethra will often increase more than one-tenth of a second prior to the increase in bladder pressure. In women with stress incontinence, the bladder pressure may rise first. The effect of a stretched endopelvic fascia on this difference in timing can be understood with reference to FIGS. 4A and B.

FIG. 4A schematically illustrates a simplified theoretical pelvic support system for a woman with stress incontinence. When pressure pulse P first begins to act on urethra U, the bladder, bladder neck, and urethra are disposed at initial position 30. As endopelvic fascia stretches significantly under the effects of pressure pulse P, there is a significant time delay between initiation of the pressure pulse and transmission of a closing force against urethra U. For example, urethra U may be closed by transmission of pressure pulse P between one-tenth and one-half second after pulse is imposed on the bladder. Hence, leakage would occur during this time delay.

This situation is different for a continent woman having the simplified theoretical pelvic support system illustrated in FIG. 4B. In this case, endopelvic fascia EF stretches much less under the influence of pressure pulse P, so that the time delay between initiation of the pressure pulse and transferring sufficient force to urethra U to effect closure is significantly less. More specifically, an increase in the modulus of elasticity of the endopelvic fascia and the pelvic support system shortens the response time of the tissue system to momentary stress. By treating the endopelvic fascia to increase its stiffness, the decent time of the pelvic viscera during a cough will be much shorter than an untreated, highly elastic tissue.

It should be noted that the continent woman's support structure schematically illustrated in FIG. 4B has an initial position 30' in which the endopelvic fascia EF is more taut than the incontinent woman's structure illustrated in FIG. 4A. In other words, excessive length of the pelvic support tissues may add to the delay and bladder movement, independently of the effects of excessive elasticity. Hence, in many cases, it will be beneficial to both increase the modulus of the endopelvic fascia and decrease its length so as to improve continence. Advantageously, the collagenous fascial tissues may be selectively contracted using many of the same system components described herein, often by heating this collagenous tissue to a slightly higher temperature than that used to promote scar tissue formation. Systems and methods for selectively contracting endopelvic fascia and other collagenous support structures are described more fully in co-pending U.S. patent application Ser. Nos. 09/133, 496 and 08/910,370, previously incorporated herein by reference.

Figure 5:
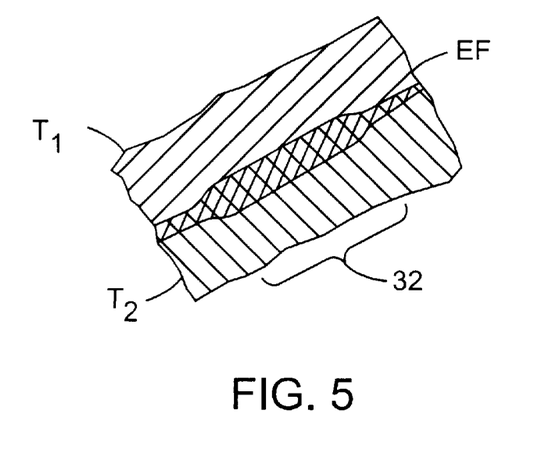
FIG. 5 is a cross-section view through an endopelvic fascia layer which has been treated according to the principles of the present invention to reduce the elasticity of the pelvic support system.

Referring now to FIG. 5, a selective target region 32 of endopelvic fascia EF has been treated to enhance a modulus of elasticity of the endopelvic fascia, and thereby of the pelvic support system. The increase in modulus of the fascial tissue may be a result of denaturing of the collagen and adjacent muscle fibers. These injured tissues are reinforced and/or replaced by stiff scar tissue. Thickening of the tissue may occur over time, due to stimulation of scar tissue and/or smooth muscle cell proliferation caused by the tissue injury. The increase in modulus may also be the result of tissue shrinkage. Shrinkage of tissues may increase the thickness of the fascial tissue plane, further enhancing the effective increase in modulus of the support structure.

The increase in the modulus of elasticity of endopelvic fascia EF has at least two distinct effects. One effect is to transfer stress from the target treatment region 32 to adjoining structures. Stress that would normally be distributed and absorbed as strain throughout the fascial surface becomes concentrated in the untreated, higher elasticity areas. Hence, if the endopelvic fascial on either side of a fascia tissue plane supporting the urethra is treated and stiffened at locations laterally displaced from the urethra (so as to avoid nerve damage to the urethra), the pressure on the fascial plane will result in higher stress on the urethra after treatment.

A second effect of local increases in the modulus is to shorten the response time of a structural tissue plane to momentary stress. This concept can be visualized using a simple example: if one were to stop a falling bowling ball with either a steel cable or a rubber band, it is obvious that the stiffer steel cable would stop the ball more quickly. Similarly, treated fascial tissue planes which have been locally or globally stiffened with scar tissue will stop the decent of the pelvic viscera during a cough much more quickly than untreated, highly elastic tissues.

Optional modalities for promoting the growth of scar tissue so as to enhance the modulus of endopelvic fascia EF between first and second tissues $T_1$, $T_2$ include the application of thermal energy (for example, through direct thermal conduction), the application of electrosurgical energy, the directing of laser energy (preferably $CO_2$ laser energy) onto the fascia, the focusing of ultrasound or microwave energy, or the like. For applying these or other forms of energy to the endopelvic fascia EF, the endopelvic fascia may be accessed surgically, preferably using minimally invasive surgical techniques so as to apply the energy directly to a surface of the endopelvic fascia. Alternatively, it may be possible to direct at least some of these forms of energy through an intervening tissue, as described more fully in co-pending U.S. patent application Ser. No. 09/288,865, the full disclosure of which is incorporated herein by reference.

Still further alternative mechanisms for promoting the formation of scar tissue so as to enhance the modulus of endopelvic fascia EF include the use of bioactive agents, such as local drug delivery to target region 32, the application of sclerosing agents to harden the tissue (such as absolute ethanol, silver nitrate, ethanolamine oleate, polidocanol, and/or N-butyl-2-cyanoacrylate), the application of pleurodesis agents, the application of causticcompounds, the use of growth factors, or the delivery of surgical sealants.

Figure 6A:
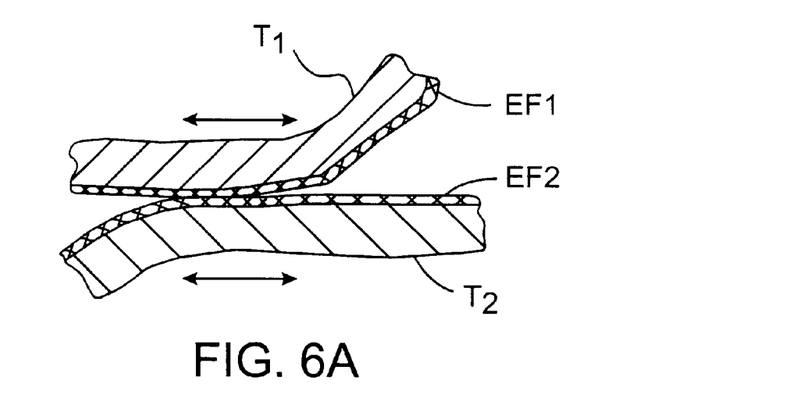
FIGS. 6A–C illustrate an alternative mechanism for enhancing the structural support of the pelvic support system by attaching two layers of endopelvic fascia which normally slide against each other.
Figure 6B:
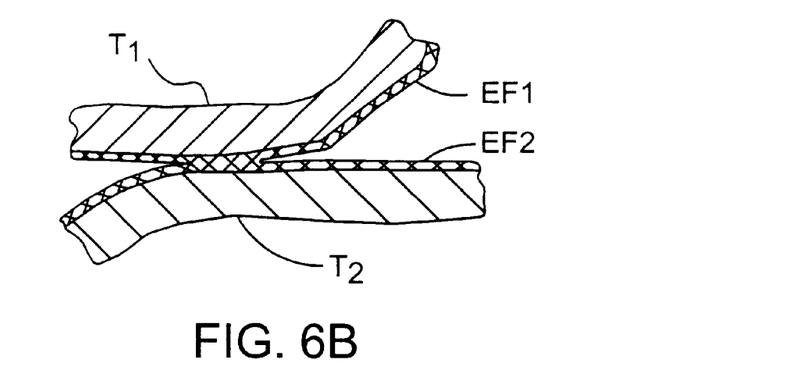
Figure 6C:
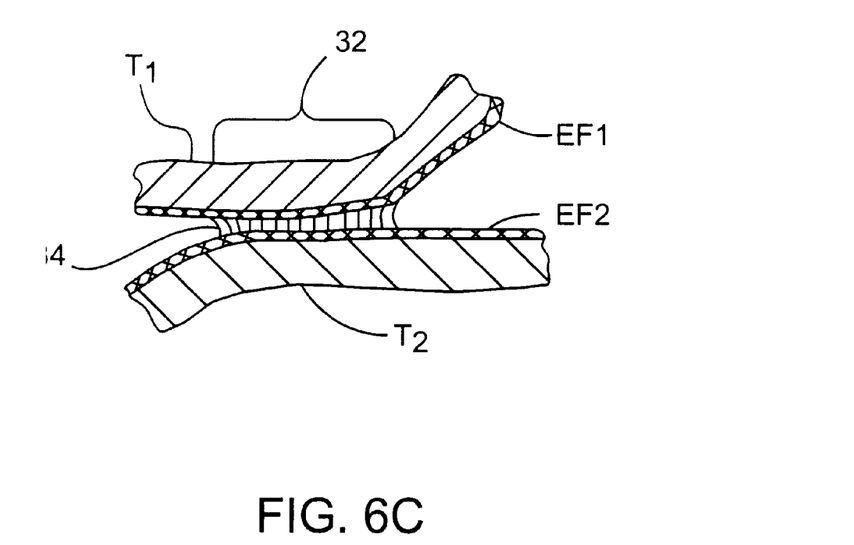

A still further alternative mechanism for increasing the overall support provided by the pelvic support system can be understood with reference to FIGS. 6A–C. As illustrated in FIG. 6A, a first tissue $T_1$ has a first endopelvic fascial layer EF1 attached thereto. Similarly, a second tissue $T_2$ has a second endopelvic fascial layer EF2, and the second endopelvic fascial layer is normally free to slide relative to first endopelvic fascial layer EF1. These fascial planes slide freely with respect to the adjoining fascial layers to allow the visceral organs to expand and contract. However, if there is inadequate support for the genitourinary tract, the motion may become extreme and result in, amongst other conditions, incontinence and/or prolapse.

As illustrated in FIGS. 6B and 6C, joining fascial layers EF1 and EF2 reduces the motion available within the pelvic support system, and restricts movement of the pelvic viscera. The treatment may be targeted to restrict the motion of organs away from their desired support locations, for example. by manipulating tissues $T_1$ and $T_2$ so that they are disposed at a desired relative position at the time of attachment.

Several distinct mechanisms are available for attachment of endopelvic fascial layers EF1 and EF2, as can be understood with reference to FIGS. 6B and C. As illustrated in FIG. 6B, acute attachment between the fascial layers may be provided by heating the fascial layers sufficiently to fuse the two collagenous tissue planes. In time, a chronic healing response to this initial fusing will result in permanent attachment due to the growth of highly cross-linked collagenous tissue spanning the previously separated endopelvic fascial layers, as illustrated in FIG. 6B.

Another chronic response to tissue injury is the development of surgically induced adhesions between tissue planes. Adhesions may occur even in locations where acute fusion of planes was not effected. In many cases, thermal damage to the surface of an endopelvic fascial tissue plane is sufficient to stimulate growth of adhesions.

In many pelvic surgeries, prevention of adhesion formation is a significant goal. Unintended adhesions are generally a source of patient discomfort, and may even cause dysfunction. Nonetheless, by intentionally promoting the controlled growth of site-specific adhesions between endopelvic fascial layers EF1 and EF2, the pelvic support system of the urethra can be significantly enhanced by allowing the transmission of forces along additional load paths. This can result in significant patient benefit where adhesions 34 at target location 32 serve to support the pelvic viscera, as illustrated in FIG. 6C. A variety of pleurodesis agents might be applied on, and/or between the fascial layers to cause fibrosis and adhesion formation, including talcum, tetracycline and derivatives, bleomycin, sodium hydroxide, blood, mitomycin, doxycycline, mitoxatrone, and/or dilute acids. Adhesion formation may also be promoted by the application of other bioactive agents described herein, by direct or remote transmission of energy, by mechanical trauma, or by combinations of these techniques.

Fascial layers EF1 and EF2 may comprise a variety of tissue structures, as generally described above. Suitable fascial layers which might be attached together so as to enhance structural support and inhibit incontinence include the periurethral fascia and the levator fascia.

Figure 7A:
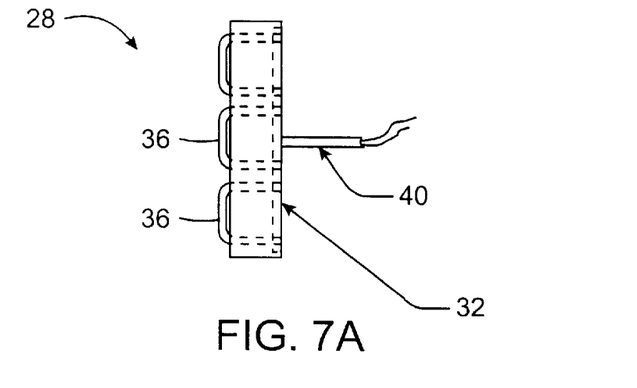
FIGS. 7A–C illustrate a static tissue treatment probe for reducing the elasticity and/or fusing fascial tissues using radio frequency energy, and methods for its use.
Figure 7B:
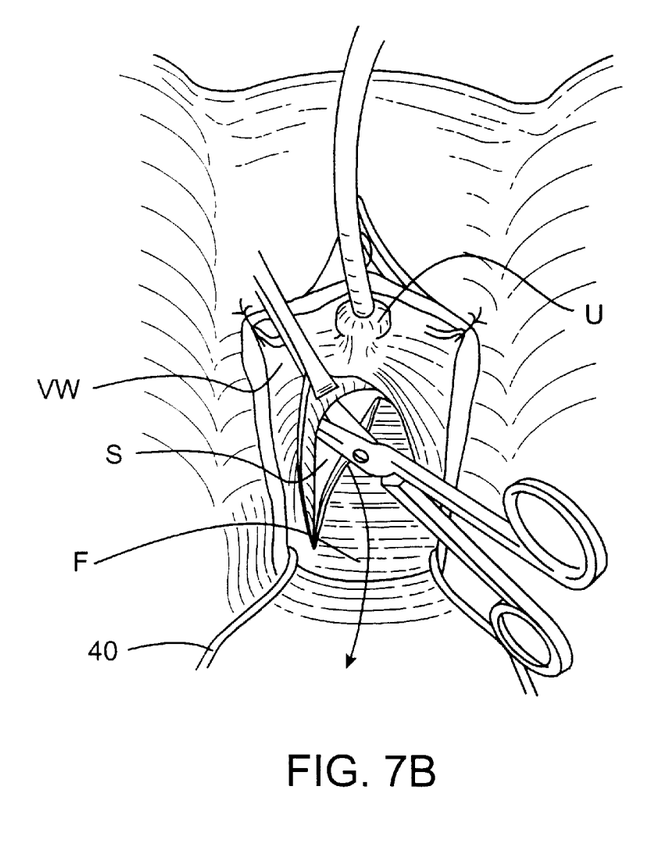
Figure 7C:
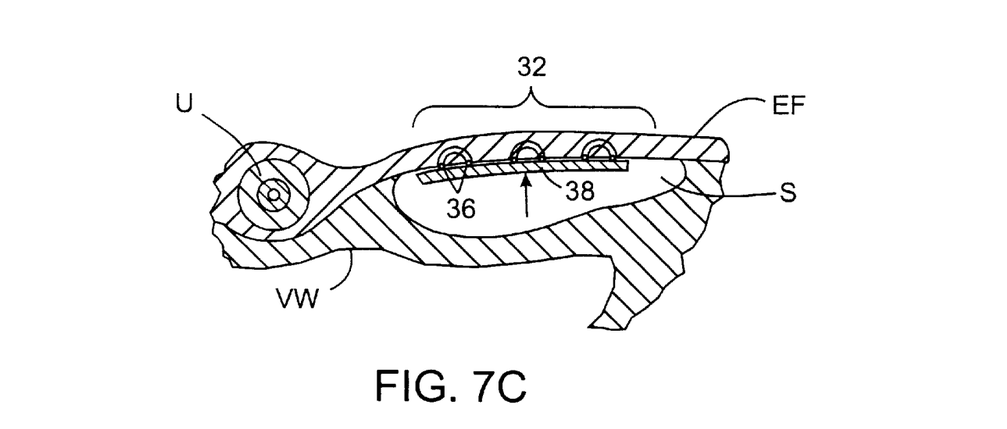
Figure 10:
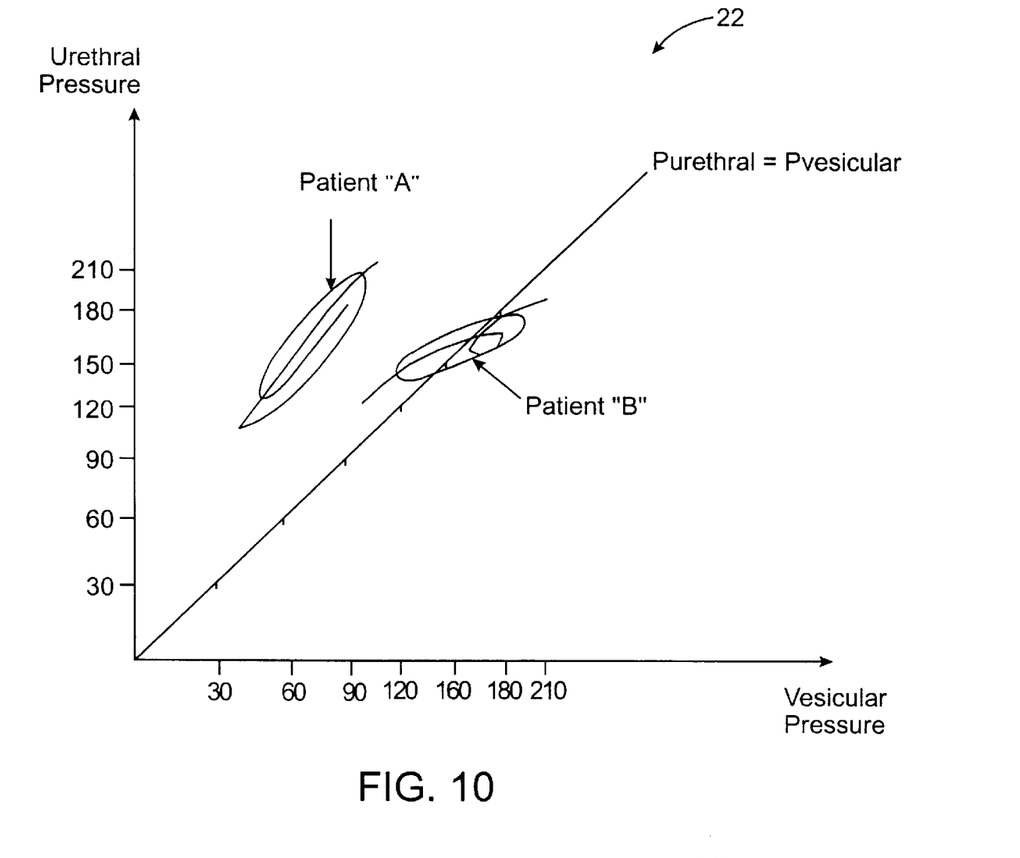
FIG. 10 is a graphical output showing a change in urethral pressure relative to a change in vesicular pressure for determine a desired change in elasticity of a pelvic support system.

Probe 28 of the system of FIG. 10 is illustrated in more detail in FIG. 7A, while methods for its use can be understood with reference to FIGS. 7B and 7C. Probe 28 includes an array of electrode pairs 36 mounted to a probe body 38. Probe body 38 may optionally be supported on a shaft 40, which will typically contain the wires coupling electrode pairs 36 to power supply 26 (see FIG. 1). Electrode pairs 36 are selectively energized by the processor of system 10, so as to transmit sufficient energy to the endopelvic fascia to effect the desired treatment. Hence processor 20 can tailor the treatment for a specific patient's diagnosis, for example, by varying the area of target region 32 so as to stiffen the endopelvic fascia layer sufficiently to maintain the urethral pressure above the vesicular pressure throughout a pressure pulse.

As explained in more detail in application Ser. No. 09/170,767 case, electrodes 36 indirectly engage surface S of endopelvic fascia EF on either side of urethra U. Optionally, the probe may include temperature sensors so as to provide a feedback signal FS to processor 20 so as to maintain the temperature of the endopelvic fascia within a target temperature range. Optionally, the target temperature range may be sufficient to promote scar tissue formation and/or attachment of the endopelvic fascial layer, and may be insufficient to induce shrinkage of the endopelvic fascia. Alternatively, both scar tissue formation and shrinkage may be effected simultaneously. Preferably, probe 28 is used in a static position so that the treatment area is controlled by processor 20 via switching unit 29 selectively applying power to some or all of electrode pairs 36, the number and location of electrode pairs, the heat time, and the heat temperature being sufficient to achieve the desired result. FIG. 7B illustrates an optional method for accessing surface S of endopelvic fascia EF transvaginally, by displacing a flap F from the vaginal wall VW with the assistance of a weighted speculum 40.

Figure 8A:
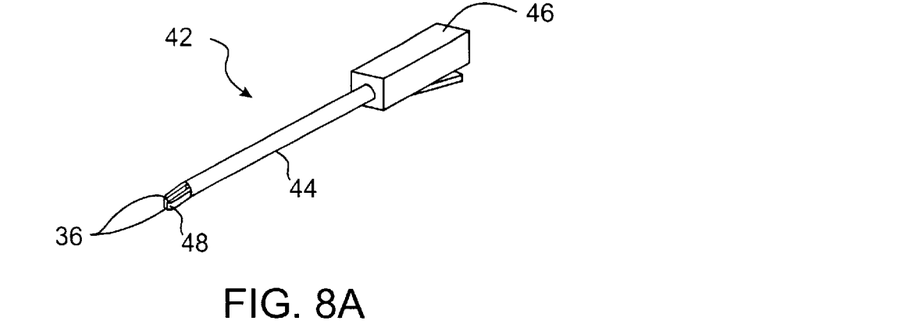
FIGS. 8A and B illustrate an alternative probe and method for its use to reduce the elasticity of endopelvic fascia by promoting the formation of scar tissue, and/or for promoting the attachment of two fascial layers together.
Figure 8B:
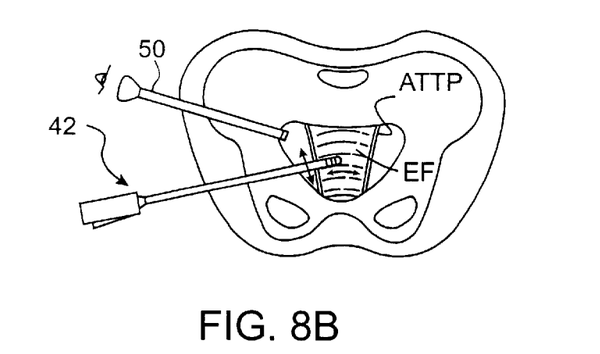

A laparoscopic device and method for directly heating endopelvic fascia EF can be understood with reference to FIG. 8A and B. Laparoscopic probe 42 includes a a shaft 44 supporting an electrode pair 36 relative to handle 46. A variety of electrode pair configurations might be used, as more fully described in co-pending U.S. patent application Ser. No. 08/910,370. Preferably, a port 48 will be disposed adjacent and/or between electrodes 36 to allow a small amount of irrigation flow before and/or during the treatment. This irrigation flow may comprise a conductive fluid such as saline or a non-conductive fluid, and will ideally be sufficient to avoid the accumulation of residue on the electrode pair surfaces. Suitable flow rates will often be in a range from about 0.5 cc/min. to about 10.0 cc/min.

Laparoscopic probe 42 will generally be used in a laparoscopic procedure using a superior approach, typically under the direction of a laparoscope 50 inserted near the patient's mid-line (for example, adjacent the belly button). Handle 46 is manipulated so as to "paint" bipolar electrode 36 across the endopelvic fascia surface until the target region has been sufficiently heated.

Figure 9:
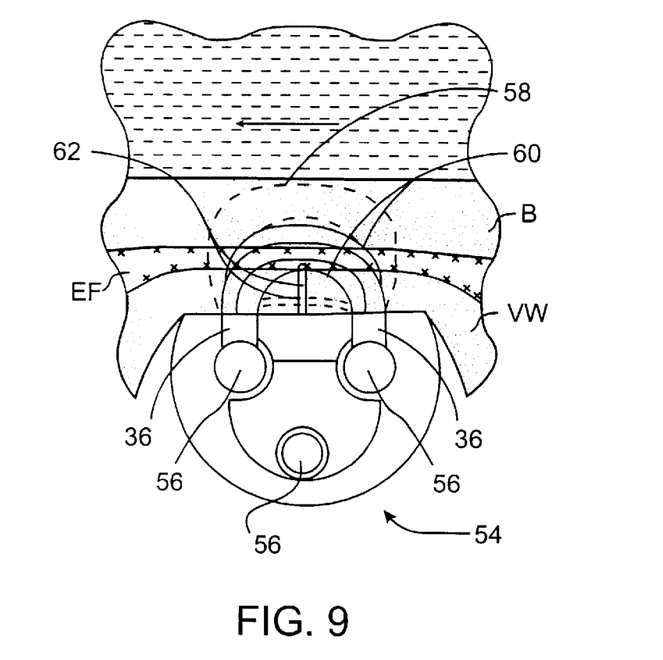
FIG. 9 is a cross-sectional drawing showing a noninvasive probe directing radio frequency current through a cooled intermediate tissue so as to promote the formation of scar tissue along an endopelvic fascia layer.

FIG. 9 illustrates a still further alternative probe for use with the system of FIG. 1. In this embodiment, a transvaginal bipolar probe 54 includes an electrode pair 36 which is cooled by fluid conduits 56. The fluid conduits cool the intervening tissue between bipolar probe 54 and endopelvic fascia EF via electrodes 36, and via the probe surface between the electrodes. Similarly, the tissue disposed beyond the endopelvic fascia (in this case a wall of bladder B) is cooled, here by circulation of a cooled solution within the bladder. Once the intervening tissue of the vaginal wall VW (and the bladder B beyond the target region of endopelvic fascia EF) are cooled sufficiently, RF current is transmitted between the electrodes to heat the endopelvic fascia. Advantageously, the pre-cooling can redirect the current flux 58 from the intervening and adjacent tissues to a desired flux pattern 60. Feedback on the pre-cooling and heating temperatures may be provided by needle-mounted temperature sensors 62 mounted to the probe, and/or by temperature sensors mounted to the probe surface.

Referring now to FIG. 10, pressuregram 22 is illustrated in more detail. Generally, a patient will remain continent so long as urethral pressure $P_u$ remains higher than vesicular pressure $P_v$. Pressuregram 22 traces the changes in urethral and vesicular pressure during a pressure pulse, such as during a cough. For patient "A", the trace of these pressures throughout the pressure pulse or pulses remains above a line indicating the pressures are equal, so that patient "A" has remained continent throughout the stress event. In fact, the slope of the pressuregram appears to be at or above unity, so that it appears that patient "A" will remain continent for larger pressure pulses.

The pressuregram of patient "B" does not remain above the $P_u=P_v$ line. Hence, at some point during the pressure pulse, the vesicular pressure is greater than the urethral pressure, and leakage may occur. To increase the slope of pressuregram trace for patient "B", the support provided by the patient's pelvic support system may be enhanced as described hereinabove. Optionally, the modulus of elasticity of one or more of the support tissues may be enhanced by promoting scar tissue formation. This will increase the slope of patient "B's" pressure pulse trace. The support tissue may, either alternatively or in combination with modulus changes, be enhanced by attaching adjacent tissue planes together, or by selectively shrinking support tissues. These latter treatments may increase the urethral pressure relative to the vesiculair pressure, moving the pressuregram pulse trace farther from the unity line.

Advantageously, the treatment of the present invention may be tailored based on the pressuregram of a particular patient. For example, scar tissue formation may be modulated based on the desired increase in pressuregram pulse slope for a particular patient by varying the area treated and/or amount of treatment (and hence scar tissue formation) for a given area, with increasing changes in pressuregram slope generally provided by increasing treatment quantity. Similarly, selective shrinking may help increase the height of the pressuregram pulse trace above the unity line (at which urethral and vesicular pressures are equal).

Figure 11:
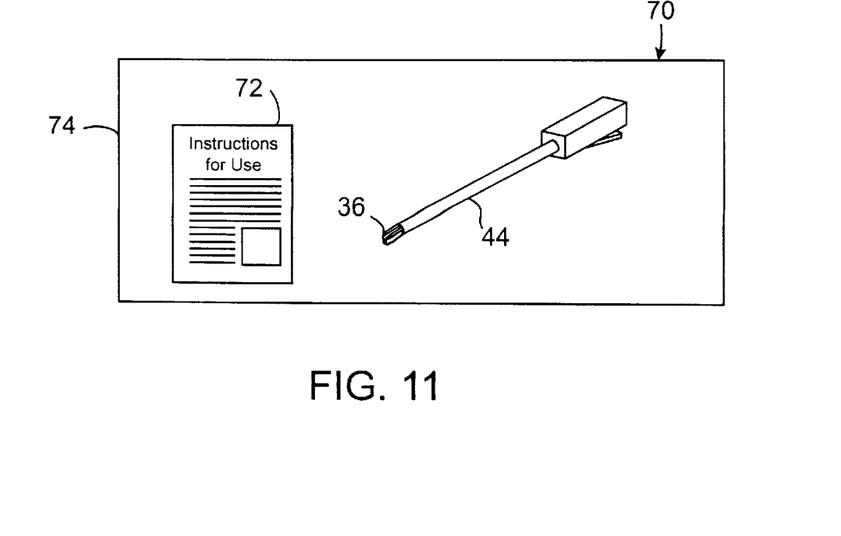
FIG. 11 schematically illustrates a kit including a probe and instructions for its use to enhance the support of a tissue support system by reducing a modulus of elasticity of a support tissue, and/or by affixing adjacent support tissues together.

Referring now to FIG. 11, a kit 70 for treating incontinence includes laparoscopic probe 42 and instructions for its use 72 within packaging 74. Kit 70 may include any of the probes described hereinabove, while instructions for use 72 will generally describe method steps for effecting any of the methods of the present invention. Packaging 74 may comprise a sterile package, and/or probe 42 may be separately packaged in a sterile container within kit 70. Instructions for use 72 may be at least in part disposed on packaging 74 or packaging for probe 42, and the instructions may be in the form of a tangible machine readable code or analog information such as a computer disk, a video tape, a CD ROM, or the like.

While the exemplary embodiments of the present invention have been described in some detail, by way of example and for clarity of understanding, a variety of changes, modifications, and adaptations will be obvious to those of skill in the art. Hence, the scope of the present invention is limited solely by the appended claims.

What is claimed is:

1. A method for treating incontinence, the method comprising reducing an elasticity of a pelvic support tissue system along a length of the tissue sufficiently so that the tissue inhibits incontinence, wherein the tissue is loaded along the length under an incontinence-event stress pulse, and wherein the elasticity of the tissue is reduced without significantly reducing the length.

2. The method of claim 1 wherein the elasticity is reduced as a result of delivering energy or an active agent to the pelvic support tissue.

3. The method of claim 1, wherein the elasticity reducing step comprises promoting scarring of a fascial tissue supporting the urethra or bladder, and wherein the scarring increases a modulus of elasticity of the fascial tissue so that the fascial tissue inhibits incontinence.

4. The method of claim 3, wherein the promoting scarring step comprises directing the energy into the fascial tissue so as to injure the fascial tissue without ablating the fascial tissue.

5. The method of claim 4, wherein the directing energy step heats the fascial tissue without significantly shrinking the fascial tissue.

6. The method of claim 4, wherein the directing energy step comprises transmitting RF current from at least one electrode to the fascial tissue.

7. The method of claim 6, further comprising irrigating the fascial tissue with sufficient fluid to avoid fouling of the electrode when the transmitting electrode moves over the fascial tissue.

8. The method of claim 1, wherein the elasticity reducing step comprises applying at least one element selected from the set containing laser energy, focused ultrasound energy, microwave energy, a caustic composition, a pleurodesis agent, a sclerosing agent, and a growth factor.

9. The method of claim 1, wherein the tissue comprises a member selected from the group consisting of: anterior sacro-coccygeal ligament; arcus tendineus fasciae pelvis; fasciae of the obturator internus muscle; the arcs tendineus levator ani; bulbocavernosus muscle; ischiocavernosus muscle; urethrovaginal sphincter; m. compressor urethrae muscle; m. sphincter urethrovaginal muscle; structures of the bladder and urethra; urethrovesical fascia; detrusor muscle; pubo-coccygeus muscle; structures of the vagina; vagino-uterine fascia; lamina propria; pubo-urethral or puboprostatic ligaments; pubo-vesicle ligament and posterior pubo-urethral or pubo-prostatic ligament; pubovesicle muscle; pubocervical fascia; structures of the uterus; round ligament; sacrouterine ligament; and broad ligament; structures cf the bowel; rectal fascia and Mackenrodt's ligament.

10. A method for treating incontinence, the method comprising:

reducing an elasticity of a pelvic support tissue system, the tissue system comprising a fascial tissue supporting the urethra or bladder, by promoting scarring of the fascial tissue, the scarring increasing a modulus of elasticity of the fascial tissue without significantly shrinking the fascial tissue and the tissue system so that the fascial tissue and the tissue system inhibit incontinence, wherein the elasticity is reduced as a result of delivering energy to the fascial tissue so as the heat the fascial tissue to a temperature in a range from 45 to below 60° C.

11. A method for treating incontinence, the method comprising:

reducing an elasticity of a pelvic support tissue system sufficiently so that the tissue system inhibits incontinence, wherein the elasticity is reduced, without significantly shrinking the tissue system, by directing energy into a fascial tissue of the tissue system so as to injure the fascial tissue without ablating the fascial tissue, and so as to promote scarring of the fascial tissue, the fascial tissue supporting a urethra or bladder, the scarring increasing a modulus of elasticity of the fascial tissue so that the fascial tissue inhibits incontinence, the directing energy step comprising transmitting RF current from at least one electrode to the fascial tissue; and maintaining an intermediate tissue disposed between the electrode and the fascial tissue at a temperature lower than a treatment temperature of the fascial tissue by cooling the intermediate tissue with the electrode, wherein the electrode transmits the RF current via the cooled tissue to the fascial tissue.

12. A method for treating incontinence, the method comprising:

reducing an elasticity of a pelvic support tissue system along a length of the tissue sufficiently so that the tissue inhibits incontinence, wherein the tissue is loaded along the length under an incontinence-event stress pulse, and comparing a change in urethral pressure relative to a change in vesicle pressure, and tailoring an incontinence therapy in response to the comparing step to maintain the urethral pressure above the vesicle pressure throughout the incontinence-event stress pulse.

13. A method for treating incontinence, the method comprising promoting attachment between a first tissue and a second tissue with energy or an active agent, the second tissue slidingly engaging the first tissue prior to attachment so that the attachment limits motion between the first and second tissues and the limited motion inhibits incontinence.

14. The method of claim 11, wherein the attachment promoting step comprises directing sufficient energy to an interface between the first tissue and the second tissue to injure a surface of a fascial tissue without ablating the fascial tissue.

15. The method of claim 9, wherein the directing energy step comprises transmitting RF current from at least one electrode to the fascial tissue.

16. The method of claim 13, further comprising irrigating the fascial tissue surface with sufficient fluid to avoid fouling of the electrode when the transmitting electrode moves over the fascial tissue surface.

17. The method of claim 13, further comprising cooling the electrode sufficiently to maintain a tissue disposed between the electrode and the fascial tissue surface at a temperature lower than a treatment temperature of the fascial tissue surface.

18. The method of claim 9, wherein the injured fascial tissue surface is acutely fused with the second tissue by heat.

19. The method of claim 16, wherein collagen of the fused first and second tissues is cross-linked during healing.

20. The method of claim 9, wherein the attachment promoting step results in formation of adhesions between the first and second tissues.

21. The method of claim 13, wherein the first tissue is selected from a group consisting of: anterior sacro-coccygeal ligament; arcus tendineus fasciae pelvis; fasciae of the obturator internus muscle; the arcs tendineus levator ani; bulbocavernosus muscle; ischiocavernosus muscle; urethrovaginal sphincter; m, compressor urethrae muscle; m, sphincter urethrovaginal muscle; structures of the bladder and urethra; urethrovesical fascia; detrusor muscle; pubococcygeus muscle; structures of the vagina; vagino-uterine fascia; lamina propria; pubo-urethral or puboprostatic ligaments; pubo-vesicle ligament and posterior pubo-urethral or pubo-prostatic ligament; pubovescile muscle; pubocervical fascia; structures of the uterus; round ligament; sacrouterine ligament; structures of the bowel; rectal fascia and Mackenrodt's ligament.

22. The method of claim 16, wherein the second tissue is also selected from the group.

23. The method of claim 11, wherein the attachment promoting step comprises applying at least one element selected from the set containing laser energy, focused ultrasound energy, microwave energy, a caustic composition, a pleurodesis agent, a sclerosing agent, a growth factor, a biomaterial mesh, and a surgical sealant.

24. A method for treating incontinence, the method comprising:

measuring a urethral pressure and a vesicle pressure during a stress;

comparing a change in the measured urethral pressure relative to a change in the measured vesicle pressure; and reducing an elasticity of a pelvic support system in response to the comparing step sufficiently that the urethral pressure will remain greater than the vesicle pressure during stress.

25. A system to treat incontinence, the system comprising:

a probe for delivering energy or an active agent to a pelvic support tissue so as to reduce an elasticity of the pelvic support tissue;

a control system coupled to the probe, the control system limiting the delivery from the probe to avoid collateral damage;

a urethral pressure sensor;

a vescile pressure sensor; and a processor coupled to the urethral pressure sensor and the vescile pressure sensor, the processor generating an output indicating a change in urethral pressure relative to a change in vesicle pressure.

* * * * *